United States Patent [19]

Vildgrube et al.

[11] Patent Number: 4,464,119
[45] Date of Patent: Aug. 7, 1984

[54] METHOD AND DEVICE FOR CORRECTING SPEECH

[76] Inventors: Georgy S. Vildgrube, prospekt M. Toreza, 13, kv. 47; Boris N. Kutuzov, prospekt Engelsa, 127, kv. 55; Valery N. Sokolsky, poselok Pesochny, ulitsa Leningradskaya, 70, korpus 2, kv. 8; Leon Y. Missulovin, ulitsa Korablestroitelei, 23, kv. 247; Boris A. Kotov, ulitsa Skorokhodova, 24, kv. 16, all of Leningrad, U.S.S.R.

[21] Appl. No.: 320,078

[22] Filed: Nov. 10, 1981

[51] Int. Cl.³ .............................................. G09B 19/04
[52] U.S. Cl. ....................................... 434/185; 381/56
[58] Field of Search ................... 434/116, 185; 381/56

[56] References Cited

U.S. PATENT DOCUMENTS 3,566,858  3/1971  Larson ............................ 434/185 X
3,920,903  11/1975  Beller ............................. 434/185 X

OTHER PUBLICATIONS

R. Pollock et al., "A Solid State Delayed Auditory Feedback System", Biomedical Engineering, Dec. 1976, pp. 413-414.
Russian Article "The Method of Using the Apparatus EKHO in the course of Complex Treatment of Stammering"; 1979.

Primary Examiner—A. D. Pellinen
Assistant Examiner—James L. Dwyer
Attorney, Agent, or Firm—Fleit, Jacobson, Cohn & Price

[57] ABSTRACT

A method of correcting the speech of a person affected by stammering comprises applying to the hearing organ of the person through an audio signal transmission channel his own speech delayed in time. The application of the speech is carried out in a frequency range the upper frequency limit of which is from 0.6 to 1.5 kilohertz. The audio signal transmission channel is blocked during the pauses between the speech fragments pronounced by the person.

A device for correcting speech comprises a microphone, a delay unit and an earphone, all connected in series, an adjusting element for adjusting the frequency spectrum of the signal transmitted from the microphone to the earphone, a switching circuit for interrupting the transmission of signal from the microphone to the earphone, and a threshold circuit having its input connected to the microphone and its output connected to the control input of the switching circuit.

3 Claims, 1 Drawing Figure

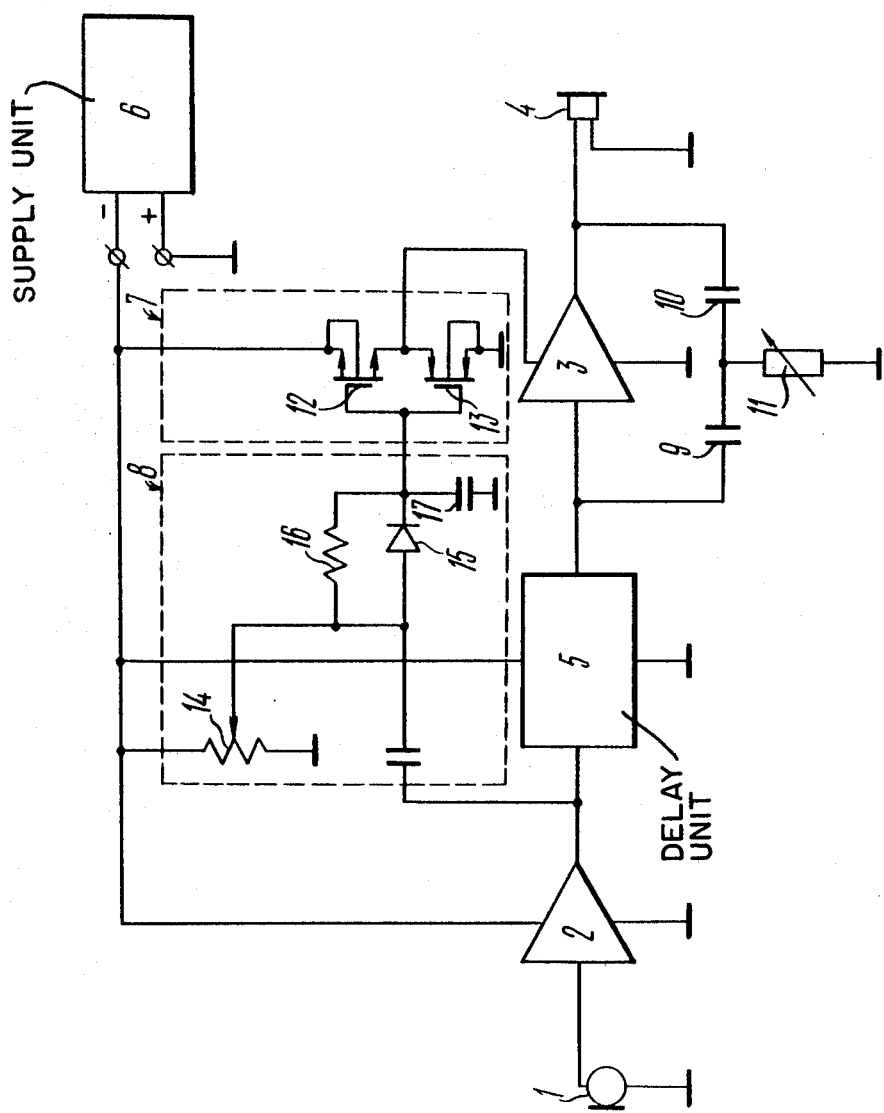

METHOD AND DEVICE FOR CORRECTING SPEECH

FIELD OF THE INVENTION

The present invention relates to methods and devices for correcting speech defects, and more particularly to methods and devices for correcting the speech of a person affected by stammering.

The present invention can be used in medical practice for treatment of logoneuroses.

BACKGROUND OF THE INVENTION

Various methods are used to correct the speech of persons affected by stammering. One of such methods consists in applying to the hearing organ of the person through an audio signal transmission channel his own speech delayed in time (cf. "Primenenie apparata "Ekho" pri ustranenii zaikaniya", Leningrad, 1979, p.p. 8-9). When this method is employed, the speaking person hears the words pronounced by himself with a time delay in relation to the instants at which they were spoken. Such a method makes it possible to separate the time of reception of speech from the time of utterance and thus enables the person to better concentrate on the speech fragments pronounced by him and helps him to overcome stammering. The duration of the time delay can be adjusted so as to choose the amount of delay most suitable for a given person.

According to the known method, application of the person's speech to his hearing organ is carried out in the relatively wide frequency range from 0.4 to 3 kilohertz, which provides a fairly high intelligibility of the speech signal supplied to the hearing organ of the person, as well as the conveyance of the timbre and intonation (emotional colouring) of the speaking person's voice. Besides, in the course of the transmission of speech the audio signal transmission channel remaines switched on both during speech fragments and during the pauses therebetween.

Therefore, the known method provides a relatively good quality of transmission of the speech sounds, which, from the viewpoint of electroacoustics, is an asset. However, as the therapeutic practice has shown, such speech transmission is not optimal as far as the treatment of stammering is concerned. This is due to the fact that, with the known method, the hearing organ of the person is supplied, during transmission of his speech, with a large amount of superfluous information which is semantically iseless, i.e. not needed by the person to perceive the meaning of the words pronounced by him, and yet has distracting influence on the person. Such superfluous information is represented by the information on the timbre and emotional colouring of the speech, as well as by the environmental noise and the internal noise of the audio signal transmission channel when both kinds of noise are not drowned by the person's speech, i.e. during the pauses between the speech fragments pronounced by the person. The application of this superfluous information increases the emotional excitement of the person, distracts his attention and hinders speech perception, which makes it difficult for the person to overcome stammering so that the correction of speech becomes less effective.

The method described above is carried out with the aid of a device comprising an acoustical-electrical transducer, a delay unit and an electrical-acoustical transducer, all connected in series (cf. "Primenenie apparata "Ekho" pri ustranenii zaikaniya", Leningrad, 1979, p.p. 8-9). The acoustical-electrical transducer is a laringophone which is to be applied to the person's throat, the electrical-acoustical transducer being an earphone which is to be positioned at the person's ear, while the delay unit is a magnetic tape recorder having its recording head connected through an amplifier to the laringophone and its reproducing head connected through another amplifier to the earphone and adapted to be moved with respect to the recording head by means of a fine adjustment screw, which makes it possible to adjust the time delay of the speech signal.

During application of the person's speech to his hearing organ, this device provides continuous transmission of a relatively wide frequency spectrum through the circuit including the electrical-acoustical transducer, the delay unit and the electrical-acoustical transducer and therefore has the same disadvantages as the known method of correcting speech described above.

SUMMARY OF THE INVENTION

It is an object of the present invention to provide a more efficient method of correcting the speech of a person affected by stammering.

It is another object of the present invention to provide a method of correcting the speech of a person affected by stammering, which method allows for reduction in the emotional excitement of the person and in distraction of his attention during application of his own speech to his hearing organ and for easier reception of his own speech.

It is yet another object of the present invention to provide a device for implementing the proposed method.

With these and other objects in view there is proposed a method for correcting the speech of a person affected by stammering, comprising applying to the hearing organ of the person through an audio signal transmission channel his own speech delayed in time, wherein, according to the invention, the application of the speech is carried out in a frequency range the upper frequency limit of which is from 0.6 to 1.5 kilohertz, and the audio signal transmission channel is blocked during the pauses between the speech fragments pronounced by the person.

With these and other objects in view there is also proposed a device for correcting the speech of a person affected by stammering, comprising an acoustical-electrical transducer, a delay unit and an electrical-acoustical transducer, all connected in series, which device, according to the invention, further comprises an adjusting element for adjusting the frequency spectrum of the signal transmitted from the acoustical-electrical transducer to the electrical-acoustical transducer, the adjusting element being adapted to reduce the upper frequency limit of the frequency spectrum of the audio signal transmitted through the circuit including the acoustical-electrical transducer, the delay unit and the electrical-acoustical transducer to a value less than 1.5 kilohertz, a switching circuit for interrupting the transmission of signal from the acoustical-electrical transducer to the electrical-acoustical transducer, and a threshold circuit having its input connected to the acoustical-electrical transducer and its output connected to the control input of the switching circuit.

With such a method and device, it is possible to reduce the amount of superfluous information which is supplied to the hearing organ of the person and which is semantically useless but has distracting influence on the person, and thereby to reduce his emotional excitement and distraction of his attention and to provide easier reception of his own speech, whereby a more effective speech correction is achieved.

It is expedient to connect the switching circuit between a supply unit and an amplifier connected between the delay unit and the electrical-acoustical transducer.

This permits the energy of the supply unit to be spent more economically.

The above-mentioned and other objects and advantages of the present invention will become more apparent upon consideration of the following detailed description of its preferred embodiments taken in conjunction with the accompanying drawing.

The invention is further explained by detailed description of its embodiments with reference to the accompanying drawing which is a schematic diagram of a device for correcting the speech of a person effected by stammering, according to the invention.

The invention is further explained by a detailed description of its embodiments with reference to the accompanying drawing.

BRIEF DESCRIPTION OF THE DRAWING

The drawing is a schematic diagram of a device for correcting the speech of a person affected by stammering, according to the invention.

DETAILED DESCRIPTION OF THE INVENTION

The method of correcting the speech of a person affected by stammering comprises applying to the hearing organ of the person through an audio signal transmission channel his own speech delayed in time, the application of the speech being carried out in a frequency range the upper limit frequency of which is from 0.6 to 1.5 kilohertz, and blocking the audio signal transmission channel during the pauses between the speech fragments pronounced by the person.

As is well known, the low-frequency components of the speech spectrum have a dominant role in conveying the meaning of speech. The high-frequency components of the spectrum are less important for conveying the meaning of speech and carry chiefly information on the timbre and intonation of speech. With the upper frequency limit of the transmitted speech signal spectrum chosen as stated above, this spectrum proves to be enough for the person to perceive the meaning of his own speech. At the same time, the absence of the high-frequency components in the speech signal prevents the person from receiving information on the emotional colouring of the speech, while the blocking of the audio signal transmission channel prevents application of extraneous noise (composed of the environmental noise and the internal noise of the transmission channel) to the hearing organ of the person during the time intervals at which this noise is not drowned by the speech.

As a result, the emotional excitement of the person during speaking and perceiving the speech is reduced and his attention is better concentrated on the process of producing speech elements, whereby a more effective speech correction is achieved. With the proposed method, the speech reception process itself is made easier because the hearing organ of the person is supplied with smaller amount of semantically useless information. Thus, because noise is not transmitted in the pauses between the speech fragments, more favourable conditions are created for the person to overcome said pauses during speaking, which is due to the fact that the sensitivity of the human ear is known to increase with decrease in the intensity of the audio signal applied thereto, which enables the person to better perceive the weak sounds which often precede the beginning of a speech fragment produced by a person affected by stammering, and thereby to overcome the pauses more quickly. Therefore a more effective speech correction is achieved.

The method described above may be implemented by means of a speech correcting device shown in the drawing.

According to the drawing, the speech correcting device comprises an acoustical-electrical transducer constituted by a microphone 1, an amplifier 2 having its input connected to the microphone 1, an amplifier 3, an electrical-acoustical transducer constituted by an earphone 4, and a delay unit 5 connected between the output of the amplifier 2 and the input of the amplifier 3. The device further comprises a supply unit 6 connected to the amplifier 2 and to the delay unit 5, a switching circuit 7 connected between the supply unit 6 and the amplifier 3, and a threshold circuit 8 having its input connected through the amplifier 2 to the microphone 1 and its output connected to the control input of the threshold circuit 7. The amplifier 3 has a negative feedback loop composed of capacitors 9 and 10 connected in series between the output and input of the amplifier 3 and of an adjustable resistor 11 connected between the point of connection of the capacitors 9 and 10 and ground.

The delay unit 5 may be a magnetic tape recording device having its recording head connected to the output of the amplifier 2 and its reproducing head connected to the input of the amplifier 3. The delay unit 5 may be also constituted by a chain of charge-coupled devices.

The switching circuit 7 comprises two MOS-transistors 12 and 13 of opposite conductivity type and connected in series between the negative terminal of the supply unit 6 and ground which is connected also to the positive terminal of the supply unit 6. The amplifier 3 is connected to the negative terminal of the supply unit 6 through the transistor 12. The gates of the transistors 12 and 13 are connected to each other forming a control input of the switching circuit 7.

The threshold circuit 8 comprises a potentiometer 14 having its resistive element connected between the negative terminal of the supply unit 6 and ground, a diode 15 having its anode connected to the movable contact of the potentiometer 14 and through a capacitor to the output of the amplifier 2, a resistor 16 connected across the diode 15, and a capacitor 17 connected between the cathode of the diode 15 and ground. The output signal of the threshold circuit 8 is derived from the capacitor 17 and is supplied to the gates of the transistors 12 and 13.

In operation, the microphone 1 is placed before the mouth of a person affected by stammering, while the earphone 4 is attached to the person's ear. The microphone may be substituted by a laringophone which is then applied to the person's throat.

The sounds uttered by the person are converted by the microphone 1 into an electrical signal which is amplified by the amplifier 2 and applied to the delay unit 5. The delay unit 5 develops at its output an electrical signal which completely coincides in shape with the signal at its input but is delayed with respect to the input signal for a time period determined by the parameters of the delay unit 5. This time period may be adjusted and usually constitutes up to 200 milliseconds.

The signal from the output of the amplifier 2 is applied also to the input of the threshold circuit 8, is rectified by the diode 15 and charges the capacitor 17. As this takes place, the voltage at the capacitor 17 exceeds the threshold value, the transistor 12 of the switching circuit is biased on, while the transistor 13 is biased off, as a result of which the voltage from the supply unit 6 is applied to the amplifier 3 which provides amplification of the signal developed at the output of the delay unit 5. The signal from the output of the amplifier 3 is applied to the earphone 4 and is converted into an audio signal which is then supplied to the hearing organ of the person. Therefore the person hears the sounds of his own speech delayed for a time period determined by the parameters of the delay unit 5.

The frequency range in which the application of speech is carried out is determined by the resistance of the adjustable resistor 11 which, together with the capacitors 9 and 10, forms a frequency-dependent network whose parameters determine the upper frequency limit of the bandwidth of the amplifier 3. The parameters of the capacitors 9 and 10 and of the resistor 11 are chosen so as to permit the upper frequency limit of the spectrum of the signal transmitted through the circuit including the microphone 1, the amplifiers 2 and 3, the delay unit 5 and the earphone 4 to be reduced to a value less than 1.5 kilohertz. The limit frequency of the spectrum is taken to be the frequency at which the transmission gain for the audio signal constitutes 30% of the transmission gain at the frequency of 400 hertz. The adjustable resistor 11 is set to a position at which the most effective correction of speech is provided. As was found by the applicants, the optimum value of the upper frequency limit may be in the range from 0.6 to 1.5 kilohertz.

During the pauses between the speech fragments, e.g. words or phrases, the signal level at the output of the amplifier 2 has a relatively small value determined by the internal noise of the amplifier 2 and by the environmental noise entering the microphone 1. In such a case the capacitor 17 discharges through the resistor 16. The voltage at the capacitor 17 becomes smaller than the threshold value, which causes the transistor 12 to turn off and the transistor 13 to turn on, with the result that the supply of voltage from the supply unit 6 to the amplifier 3 is cut off, which, in turn, leads to interruption of the transmission of signal between the microphone 1 and the earphone 4, i.e. to blocking of the audio signal transmission channel. The time period after which the transmission of signal is interrupted following the end of a speech fragment is determined by the discharging time constant of the capacitor 17, which depends on the resistance of the resistor 16. As soon as a new speech fragment begins, the signal level at the output of the amplifier 2 rises and the capacitor 17 is quickly charged through the diode 15 to the voltage above the threshold value causing the transistors 12 and 13 to reverse their states and the supply voltage to be furnished to the amplifier 3. The small charging time constant of the capacitor 17 ensures transmission of the initial sounds of each speech fragment to the earphone 4, which is most important for achieving effective speech correction. The threshold value of the signal at the output of the amplifier 2 at which the transistors 12 and 13 are switched is set by the potentiometer 14.

The amplifier 2 is a voltage amplifier which consumes little energy from the supply unit 6, while the amplifier 3 is a power amplifier which consumes a relatively large amount of power from the supply unit 6. Therefore, with the delay unit 5 constituted by elements consuming little energy from a power supply, e.g. by charge-coupled devices, the employment of the switching circuit 7 arranged to disconnect the amplifier 3 from the supply unit 6 provides substantial saving of the energy consumed by the device from the supply unit 6.

While the invention is described herein in the terms of its preferred embodiments, numerous modifications may be made without departure from the spirit and scope of the invention as defined by the appended claims.

It will be readily seen that the reduction of the upper frequency limit of the audio signal spectrum transmitted through the circuit including the microphone 1, the amplifiers 2 and 3, the earphone 4 and the delay unit 5 may be achieved by a corresponding reduction in the bandwidth of any element of this circuit or of several of said elements. The switching circuit 7 may be connected between the delay unit 5 and the amplifier 3 or between the amplifier 3 and the earphone 4. To connect the switching circuit 7 before the delay unit 5 is undesirable because the lag in the switching circuit may lead to the loss of the initial sounds of speech fragments applied to the ear of the person. The switching and threshold circuits may be constituted by various conventional circuits adapted to switch on and off electric circuit elements in response to variation of a signal level with respect to a threshold value.

We claim:

1. A method of correcting the speech of a person affected by stammering with the use of an audio signal transmission channel, comprising applying to the hearing organ of said person through said audio signal transmission channel his own speech delayed in time, the application of the speech being carried out in the frequency range the upper frequency limited of which is from 0.6 to 1.5 kilohertiz, and blocking said audio signal transmission channel during the pauses between the speech fragments pronounced by said person wherein said blocking permits passage of initial fragments of the speech immediately after termination of the blocking without significant delay.

2. A device for correcting the speech of a person affected by stammering, comprising:
an acoustical-electrical transducer for converting the speech of said person into an electrical signal;
a delay unit for delaying the speech signal;
an electrical-acoustical transducer adapted to be positioned near the hearing organ of said person and connected to said acoustical-electrical transducer through said delay unit;
an adjusting element for adjusting the frequency spectrum of the signal transmitted from said acoustical-electrical transducer to said electrical-acoustical transducer, said adjusting element being operative to reduce the upper limit frequency of the frequency spectrum of the audio signal transmitted through said acoustical-electrical transducer, said delay unit and said electrical-acoustical transducer to a value less than 1.5 kilohertz;
a switching circuit for interrupting the transmission of the signal from said acoustical-electrical transducer to said electrical-acoustical transducer, said switching circuit having a control input; and a threshold circuit having an input and an output, said input of said threshold circuit being connected to said acoustical-electrical transducer, while said output of said threshold circuit is connected to said control input of said switching circuit, said switching circuit and said threshold circuit having a response time to permit passage of initial fragments of the speech immediately after termination of interruption of the speech.

3. A device according to claim 2, comprising a supply unit, and an amplifier connected between said delay unit and said electrical-acoustical transducer, wherein said switching circuit is connected between said supply unit and said amplifier.

* * * * *